(12) United States Patent
Womelsdorf et al.

(10) Patent No.: US 6,710,091 B1
(45) Date of Patent: Mar. 23, 2004

(54) NANOPARTICULATE, REDISPERSIBLE ZINC OXIDE GELS

(75) Inventors: Hermann-Jens Womelsdorf, Leverkusen (DE); Werner Hoheisel, Köln (DE); Gerd Passing, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/913,990

(22) PCT Filed: Feb. 11, 2000

(86) PCT No.: PCT/EP00/01116

§ 371 (c)(1),
(2), (4) Date: Aug. 21, 2001

(87) PCT Pub. No.: WO00/50503

PCT Pub. Date: Aug. 31, 2000

(30) Foreign Application Priority Data

Feb. 23, 1999 (DE) .......................................... 199 07 704

(51) Int. Cl.$^7$ .............................. B01F 3/12; C01G 9/02
(52) U.S. Cl. .............................. 516/33; 516/88; 516/98; 423/101; 423/102; 423/104; 423/622
(58) Field of Search .............................. 516/33, 88, 98; 423/101, 102, 104, 622

(56) References Cited

U.S. PATENT DOCUMENTS

| 5,089,248 A | * | 2/1992 | Akhtar ........................ 423/604 |
| 5,391,354 A | | 2/1995 | Petersen et al. ............. 422/129 |
| 5,716,679 A | * | 2/1998 | Krug et al. .................. 427/515 |
| 6,200,680 B1 | | 3/2001 | Takeda et al. ............... 428/402 |

FOREIGN PATENT DOCUMENTS

| JP | 4-164814 | | 6/1992 |
| JP | 7-232919 | | 9/1995 |
| WO | WO 97/24224 | * | 7/1997 |

OTHER PUBLICATIONS

Sakoharaet al, "Visible Luminescence and Surface Properties of Nanosized ZnO Colloids Prepared by Hydrolyzing Zinc Acetate", J. Phys. Chem B., vol. 102, No. 50, Dec. 1998, pp. 1016910175.*

Hilgendorff et al, "From ZnO Colloids to Nanocrystalline Highly Conductive Films", J. Electrochem. Soc., vol. 145, No. 10, Oct. 1998, pp. 3632–3637.*

Spanhel et al., "Semiconductor Clusters in the Sol–Gel Process: Quantized Aggregation, Gelation, and Crystal Growth in Concentrated ZnO Colloids", J. Am. Chem. Soc. 1991 (month unavailable) 113, pp. 2826–2833.*

Patent Abstracts of Japan, vol. 199, No. 605, corresponding to Jp 08 026823 A (Toshio Tsuchiya) Jan. 30, 1996.*

J. Phys. Chem., 92 (month unavailable) 1988, Month unknown pp. 482–487, "Photochemistry and Radiation Chemistry of Colloidal Semiconductors. 23. Electron Storage on ZnO Particles and Size Quantization", Markus Haase, Horst Weller and Arnim Henglein.

J. Phys. Chem., 90 (month unavailable) 1986, Month unknown pp. 2555–2560, "Electronic Wave Functions in Semiconductor Clusters: Experiment and Theory", Louis Brus.

Gmelins Handbuch, Vol 32, 8$^{th}$ ed. Supplementary vol. (month unavailable) 1956, Month unknown pp. 722–773 "Zinkoxyd".

* cited by examiner

Primary Examiner—Daniel S. Metzmaier
(74) Attorney, Agent, or Firm—Joseph C. Gil; Gary Matz

(57) ABSTRACT

A method for the preparation of nano size zinc oxide particles having an average primary particle diameter of less than or equal to 15 nm, which are redispersible in organic solvents and/or water, by basic hydrolysis of at least one zinc compound in alcohol or an alcohol/water mixture. The hydrolysis is carried out with substoichiometric amounts of base, based on the zinc compound. The precipitate which originally forms during hydrolysis is left to mature until the zinc oxide has completely flocculated. This precipitate is then thickened to give a gel and separated off from the supernatant phase.

6 Claims, 2 Drawing Sheets

NANOPARTICULATE, REDISPERSIBLE ZINC OXIDE GELS

FIELD OF THE INVENTION

The present invention relates to nanoparticulate, redispersible zinc oxide gels, to processes for their preparation and to their use.

BACKGROUND OF THE INVENTION

Zinc oxide is used for diverse purposes, such as, for example, as a white pigment, as a catalyst, as a constituent of antibacterial skin-protection ointment and as an activator for rubber vulcanization. Sunscreens and wood varnishes contain finely divided zinc oxide as UV-absorbing pigment.

The term "nanoparticle" is generally used to refer to particles having a diameter of less an about 100 nm.

Zinc oxide nanoparticles having particle sizes below about 30 nm are potentially suitable for use as UV absorbers in transparent organic-inorganic hybrid materials, plastics, paints and coatings. In addition, use for the protection of UV-sensitive organic pigments is also possible.

Particles, particle aggregates or particle agglomerates of zinc oxide which are greater than about 30 mn lead to scattered light effects and thus to an undesired decrease in transparency in the visible light region. For this reason, redispersibility, i.e. the convertibility of the prepared zinc oxide nanoparticles into a colloid-disperse state, is an important prerequisite for the abovementioned applications.

Zinc oxide nanoparticles having particle sizes below about 5 nm exhibit, because of the size quantization effect, a blue shift in the absorption edge (L. Brus, J. Phys. Chen. (1986), 90, 2555–2560) and are therefore less suitable for use as UV absorbs in the UV-A region.

The preparation of zinc oxide by dry and wet processes is known. The classical method of burning zinc, the dry process (e.g. Gmelin vol. 32, 8th edition, supplementary volume, p. 772 ff), generates aggregated particles having a broad size distribution. Although in principle it is possible to prepare stable dispersions by grinding procedures with the help of surface-active agents, because the shear forces which can be achieved are too low, it is not possible to obtain dispersions having average particle sizes below about 30 nm from such powders.

Particularly finely divided zinc oxide is prepared predominantly by wet chemical methods by precipitation processes. Precipitation in aqueous solution generally gives hydroxide- and/or carbonate-containing materials which have to be thermally converted to zinc oxide. The thermal post-treatment has a negative effect on the finely divided nature since the particles are subjected during this treatment to sintering processes which lead to the formation of µm-sized aggregates which can be broken down only incompletely to the primary particles by grinding.

JP-A-04 164 814 describes a process which leads, as a result of precipitation in aqueous medium at elevated temperature even without thermal post-treatment, to finely divided ZnO. The average particle size is given as 20–50 nm, with no information on the degree of agglomeration. These particles are relatively large. Even if agglomeration is minimal, this leads to scattering effects which are undesired in transparent applications.

JP-A-07 232 919 describes the preparation of ZnO particles which are 5–10,000 nm in size from zinc compounds by reaction with organic acids and other organic compounds such as alcohols at elevated temperature. The hydrolysis is carried out here such that the by-products which form (esters of the acids used) can be distilled off. The process permits the preparation of ZnO powders which are redispersible as a result of surface modification which has been carried out beforehand. However, on the basis of the disclosure of this application it is not possible to prepare particles having an average diameter of <15 nm. Accordingly, in the examples given in the application, the smallest average primary particle diameter is given as 15 nm.

EP 0 893 409 A1 describes the preparation of zinc oxide nanoparticles as in JP-A-07 232 919, except that during the precipitation of the ZnO, another metal oxide, from the groups of the Periodic Table of the Elements named "IIIB" and "IVB" in the application, aluminum and indium being given in particular by name, is coprecipitated.

Furthermore, attempts have been made to obtain ZnO directly by hydrolysis of zinc salts in alcohols (Henglein et al., J. Phys. Chem. 1988, 92, 482–487). Using NaOH as base it was not possible to obtain stable and concentrated sols ($C_{ZnO} \gg 10^{-3}$ mol/l).

The hydrolysis of zinc acetate with LiOH or tetramethylammonium hydroxide (Spanhel et al., JACS 1991, 113, No.8, 2826–2833) in alcoholic solution gave concentrated sols which, in addition to zinc oxide nanoparticles, also comprised lithium acetate or tetramethylammonium acetate, respectively, in stoichiometric amount. For this reason, firstly, cost-effective preparation is not possible since LiOH and tetramethylammonium hydroxide are relatively expensive, and, secondly, further use of the sols is severely limited since the by-products of the precipitation are not separated off. By concentrating these sols it was possible to obtain ZnO-containing gels which likewise still contained the by-products of the ZnO preparation in stoichiometric amount and were thus severely limited with regard to their further possible uses.

Other processes for the preparation of nanosize zinc oxide, such as that described in U.S. Pat. No. 5,391,354, which starts from zinc alkoxides, use expensive starting materials and are therefore uneconomical.

SUMMARY OF THE INVENTION

The object of the present invention was therefore to provide a nanosize zinc oxide which combines strong UV-absorption even in the UV-A region with excellent dispersion properties for minimal scattering To this end, it was necessary to find a simple process which is suitable for preparing nanosize zinc oxide having an average primary particle diameter between 5 and 15 nm from commercially available, cost-effective starting materials on an industrial scale at low cost in a manner which permits the zinc oxide, following preparation, to be separated off from the by-products without the particles undergoing irreversible aggregation and, following redispersion, to be prepared for further use in the form of sols without laborious grinding.

Starting from the method for the hydrolysis of zinc acetate in alcoholic media described by Henglein et al., it has now surprisingly been found that by hydrolysing zinc compounds with bases in alcohol or alcohol/water mixtures, followed by removal of the supernatant solution charged with the by-products of the precipitation, it is possible to obtain zinc oxide gels comprising zinc oxide nanoparticles having average primary particle diameters of ≦15 nm which, simply by adding suitable solvents or solvent combinations— optionally together with suitable surface modifier—sand stirring, and dispensing with grinding stages or other laborious mechanical comminution processes, can be redispersed completely to give largely primary-particle-disperse zinc oxide sols, without a significant loss in quality with regard to the monodispersity and size of the particles.

The invention therefore relates to zinc oxide gels comprising nanosize zinc oxide particles having an average primary particle diameter of ≦15 nm, water and alcohol, which are redispersible in at least one organic solvent and/or water, optionally with the addition of surface-modifying compounds, to give sols.

For the purposes of the invention, "average primary particle diameter" means the average circle-equivalent primary particle diameter of the zinc oxide particles which can be determined in a transmission electron micrograph.

The invention also relates to a process for the preparation of zinc oxide gels by basic hydrolysis of at least one zinc compound in alcohol or an alcohol/water mixture, characterized in that the precipitate which initially forms during hydrolysis is left to mature until the zinc oxide has completely flocculated, then this precipitate is thickened to a gel and separated off from the supernatant phase.

DESCRIPTION OF THE PREFERRED EMBODIMENT

Figure 1:
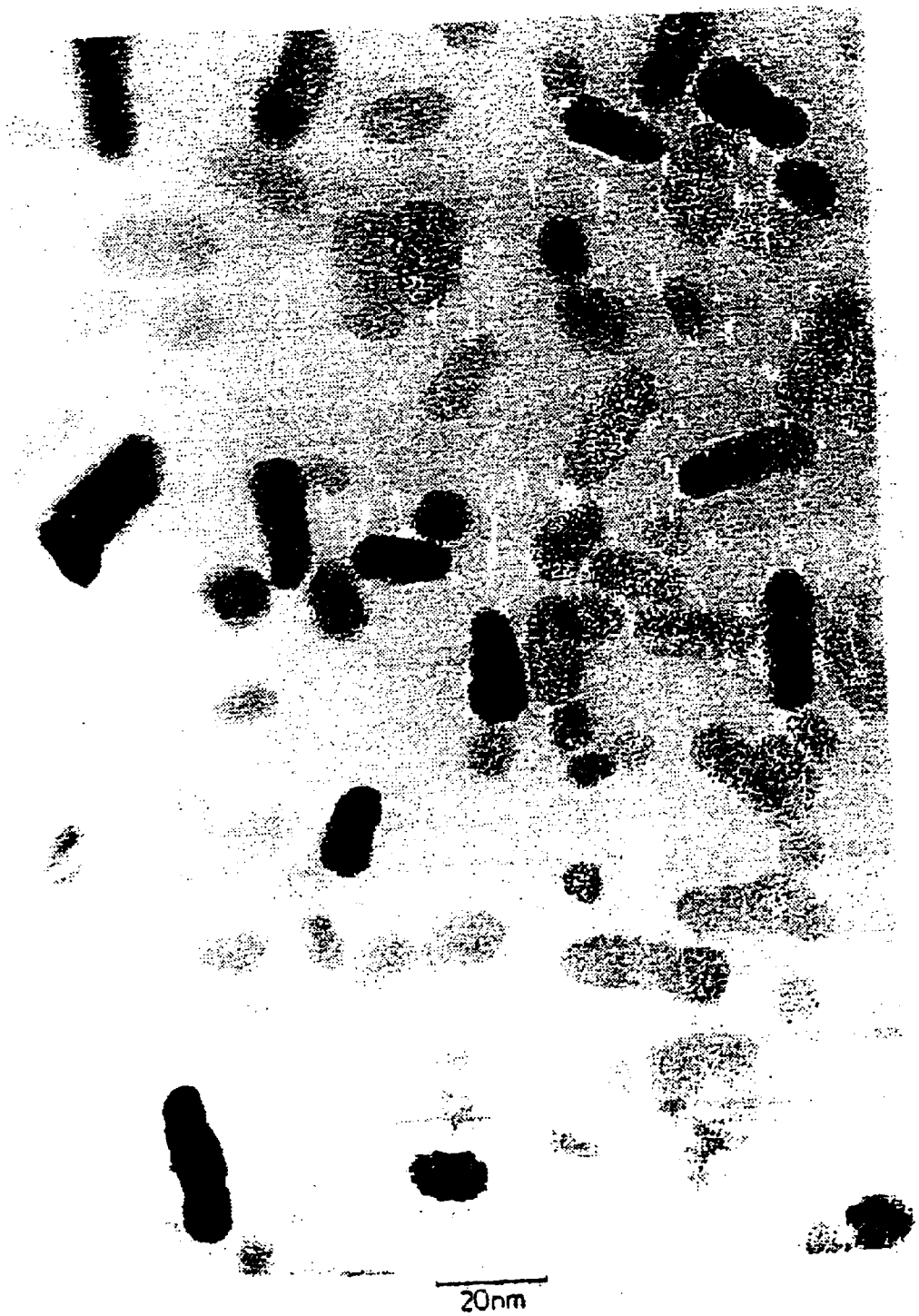
FIG. 1 is a transmission electron micrograph of a sample of the gel (A) diluted in an ethylene glycol/water mixture.

The process according to the invention is preferably carried out such that at least one zinc compound is completely or partially dissolved in alcohol or an alcohol/water mixture and hydrolysed by adding at least one base at temperatures between the freezing point of the solution and its boiling point. This produces, depending on the temperature and concentration, and optionally after a time delay, a whitish precipitate.

As soon as zinc oxide is no longer or virtually no longer in colloidal disperse form, optionally after interspersed washing steps in which, after the precipitate has settled, the supernatant is exchanged for fresh solvent the precipitate can be thickened to give a gel and separated off from the supernatant phase. To test whether any zinc oxide is still in colloidal disperse form, it is possible to filter a sample of the reaction mixture through a filter having a pore size of 0.2 μm and test the filtrate for the Tyndall effect. The precipitate can be thickened to give a gel by settling and leaving to stand, or by centrifuging, the precipitate preferably being centrifuged.

The resulting zinc oxide gel can be redispersed to give largely primary-particle-disperse sols by adding organic solvents and/or water, optionally with the addition of surface-modifying compounds. The redispersion here is preferably effected by admixing the corresponding solvent or solvent mixture with stirring.

The zinc compound used in the process according to the invention is preferably a salt-like compound which is completely or partially soluble in the chosen alcohol or water/alcohol mixture, particular preference being given to zinc acetate, and very particular preference to its dihydrate.

The alcohol used is preferably a monoalcohol, very particularly preferably methanol.

The base can be an OH- or NH-group-containing basic compound, particularly one obtainable in concentrated form and soluble in alcohol or alcohol/water mixtures. These include, in particular, sodium and potassium hydroxide and amine bases, the former being preferred. The base can either be used in solid form, for example as NaOH or KOH pellets, or in dissolved form in the process according to the invention. In a preferred embodiment of the invention, the base is added in dissolved form to the solution of the zinc salt. Hem, the base is preferably dissolved in alcohol, water or alcohol/water mixtures, particularly preferably in methanol, water or methanol/water mixtures.

The hydrolysis is preferably carried out using nonstoichiometric amounts of base, particularly preferably substoichiometric amounts, very particularly preferably with a Zn to OH ratio of from 1:1.6 to 1:1.95.

The minimal water content of the reaction mixture is determined by the water content of the starting materials used and by the amount of zinc oxide which forms. Moreover, water can be added in order to achieve particular effects, e.g. to accelerate the formation of ZnO or to improve the solubility of the starting materials.

In a preferred embodiment of the invention, more zinc salt is used than corresponds to the solubility product in the solvent used. By adding a fraction of the amount of base intended for the hydrolysis, the solubility of the zinc salts is improved without zinc oxide already being formed.

In a further preferred embodiment of the invention, dissolution of the starting materials and hydrolysis are carried out with inert-gas blanketing.

In a further preferred embodiment, the zinc compound used is a commercially available, coarsely divided zinc oxide which is reacted in an up reaction to give a suitable zinc compound, preferably zinc acetate. In a particularly preferred embodiment of the invention, this is carried out by reacting zinc oxide with glacial acetic acid in a glacial acetic acid/acetic anhydride mixture or in an alcohol/water mixture.

In a preferred embodiment of the invention, the temperature during dissolution and reaction is between 0° C. and the boiling point of the solvent used In a particularly preferred embodiment of the invention, the temperature is increased before and/or during and/or following precipitation to the boiling point of the mixture or a temperature below it.

To influence the morphology and/or the crystallinity of the zinc oxide particles, it is possible to add suitable compounds (foreign ions) before, during or after precipitation. Preference is given to compounds of the 2nd–4th main group and transition metal compounds. Particular preference is given to manganese, magnesium, silicon and aluminium compounds, very particular preference to aluminium and silicon alkoxides, aluminates and silicates. In a preferred embodimient of the process according to the invention, these compounds are added to the reaction mixture in dissolved form. Here, preferably from 0.01 to 3 mol %, based on zinc, are used.

The precipitate can be isolated, for example by decantation or by drawing off the supernatant with suction. In this connection, it is favourable to thicken the precipitate well, for example as a result of long settling times, since the redispersibility behaviour of the precipitate depends on the content of salt and solvent. If the settling time is relatively long, the precipitate thickens to give a high-viscosity gel. Particularly good thickening of the material and thus also particularly complete removal of the zinc oxide from the by-products of the precipitation is achieved by centrifugation. Here, a translucent, solid gel having a high solids content is obtained which is particularly readily redispersible.

In a further preferred embodiment, the salt content of the precipitate is, after settling, reduced by drawing off some of the supernatant with suction and adding fresh solvent. The salt content of the precipitate is particularly preferably reduced by drawing off some of the supernatant with suction and adding fresh solvent if the zinc oxide gel which forms is to be redispersible in water or alcohol/water mixtures, in particular diol and/or polyol/water mixtures, preferably with use of surface-modifying compounds, to give a sol.

The resulting zinc oxide gel can be converted into a colloid-disperse sol by suitable measures. In a preferred embodiment of the invention, this is effected by adding organic solvents, preferably polar aprotic solvents, very particularly preferably dichloromethane and/or chloroform. In a further preferred embodiment, the gel is redispersed in water. In a further preferred embodiment, the gel is redispersed in mixtures, in particular diol and/or polyol/water mixtures, preferably using surface-modifying compounds. The surface-modifying compounds are preferably nitrogen-containing compounds, particular preference being given to triethanolamine.

Grinding steps or other laborious mechanical comminution steps are not necessary.

The addition preferably takes place in a mass ratio of zinc oxide gel to solvent of from 1:0.4 to 1:10, particularly preferably in the ratio from 1:0.4 to 1:3, very particularly preferably in the ratio from 1:0.7 to 1:1.5. The mass ratios which are required to obtain a stable sol vary depending on the solvent used.

In a further preferred embodiment, the precipitate can, prior to thickening to give the gel, be converted, by adding dichloromethane and/or chloroform, into a zinc oxide sol in which the zinc oxide particles are in colloid-disperse form. This is preferably carried out after the salt content of the precipitate has previously been reduced by repeatedly settling and drawing off some of the supernatant with suction and adding fresh solvent.

The invention further relates to the use of the zinc oxide gel according to the invention or the sol produced therefrom in organic-inorganic hybrid materials, in particular for the UV protection of polymeric materials, paints and coatings, in particular for transparent applications. In addition, use for the protection of UV-sensitive organic pigments and dyes is also possible. In addition, the zinc oxide gels and zinc oxide sols according to the invention are also suitable for the matrix modification of polymers, paints and coatings and as an improved vulcanization activator for rubbers and latices.

EXAMPLES

The invention is described in more detail with reference to the examples below without being limited to these examples.

The centrifugation steps were carried out in a laboratory centrifuge from Heraeus (Variofuge RF) having a rotor with a radius of 20.4 cm.

Example 1

590 g of zinc acetate dihydrate were dissolved in 2000 g of methanol at 55° C. in a 6 l flask and a solution, conditioned at room temperature, of 302 g of potassium hydroxide pellets (84.7%) in 1000 g of methanol were added with sting. A white, voluminous precipitate immediately formed, which was left to settle for 14 h. 3165 g were then drawn off from the supernatant with suction and replaced by 1000 g of methanol. The mixture was then stirred for about 20 min. After a settling time of 75 min, a further 806 g of supernatant were drawn off with suction and replaced by 500 g of methanol. The mixture was stirred for a further 40 min, and then, after a settling time of 40 min, a further 786 g of supernatant were drawn off with suction and replaced by 500 g of methanol. After a stirring time of 30 min, the mixture was centrifuged (5500 rotations/min, 30 min). Following centrifugation, the mass of the resulting zinc oxide gel was 251 g.

The solids content of the gel was 75.3% (drying: 1 h at 130° C.). Elemental analysis revealed a zinc content of 75.7%, corresponding to 93.9% of ZnO. In addition, 0.25% of potassium, corresponding to about 0.63% of potassium acetate, were found.

An X-ray diffractogram of the dried sample indicated exclusively hexagonal zinc oxide. Evaluation of the reflections according to Scherrer revealed an average crystallite size of 6.9 nm (reflections: 100 and 002, 100 doubly weighted since identical to 010 in the hexagonal crystalline system).

Example 2

218.5 g of zinc oxide (99.8%) were introduced into a 6 litre 4-necked flask and mixed with 1200 g of methanol, 330 g of glacial acetic acid and 46.5 g of deionized water and heated to 60° C. with stirring In parallel to this, a solution of 301.68 g of potassium hydroxide pellets (84.7%) and 700 g of methanol was prepared with cooling. After the mixture present in the flask had reached 60° C., approximately 80 ml of the prepared KOH/methanol solution was slowly metered in via a dropping funnel. The mixture clarified slowly and after about 30 min was clear. Then, at 60° C., the remainder of the KOH/methanol solution was metered in over the course of 30 seconds via a dropping funnel. Considerable white turbidity immediately famed, and the temperature of the mixture increased by about 2° C. After a few minutes the mixture clarified somewhat and then again turned milky white. The heating source was then removed and the mixture was cooled in an ice bath for 20 min The stirrer was switched off at a temperature of 16° C. After about 2 hours a white sediment formed in the flask, and the supernatant was virtually clear. 2078 g were drawn off from the supernatant with suction and replaced by 750 g of methanol. The mixture was then stirred for about 60 min and then the reaction mixture was divided in the ratio 1:1. One half (A) was further processed as follows: after settling out for 14 h, the supernatant was decanted off and replaced by 375 g of methanol. The mixture was then stirred for about 50 min and then, after renewed settling out and decantation, 375 g of methanol was again added. The mixture was then stirred again for about 50 min, then centrifuged at 5500 rpm for 30 min, and the supernatant was decanted off. The gel weight was 130.6 g The solids content of the gel was 75.8% (drying: 1 h at 130° C.). Elemental analysis revealed a zinc content of 76%, corresponding to 94.6% of ZnO. In addition, 0.09% of potassium, corresponding to about 0.21% of potassium acetate, were found.

An X-ray diffractogram of the dried sample indicated exclusively hexagonal zinc oxide. Evaluation of the reflections according to Scherrer revealed an average crystallite size of 7.9 nm (reflections: 100 and 002, 100 doubly weighted since identical to 010 in the hexagonal crystalline system).

A transmission electron micrograph of a sample of the gel (A) diluted in an ethylene glycol/water mixture is shown in FIG. 1.

The other half of the reaction mixture was thickened by centrifugation at 5500 min$^{-1}$ for 30 min to give a gel. The gel weight of the gel (B) was 134.1 g.

Example 3

218.5 g of zinc oxide (99.8%) were introduced into a 6 litre four-necked flask and mixed with 1200 g of methanol, 328.5 g of glacial acetic acid and 46.5 g of deionized water and heated to 60° C. with stirring. In parallel thereto, a solution of 308.1 g of potassium hydroxide pellets (84.7%) and 700 g of methanol was prepared with cooling. After the mixture in the flask had reached 60° C., about 90 ml of the prepared KOH/methanol solution was slowly metered in via a dropping funnel. The solution clarified slowly and was clear after about 15 min. A solution of 2.8 g of aluminium tri-sec-isobutoxide in 20 g of 2-propanol were then added. The remaining KOH/methanol solution was then metered in over the course of 30 seconds by a dropping funnel. Considerable white turbidity immediately formed, and the temperature of the mixture increased by about 2° C. After a few minutes, the mixture clarified somewhat and then again tuned milky white. The healing source was then removed and the mixture was cooled in an ice bath The stirrer was switched off at a temperature of 23° C. After a settling out time of 14 h, a white sediment had formed. 1920.7 g were drawn off from the supernatant with suction and replaced by 700 g of methanol. The mixture was then stirred for about 45 min and was then divided in the ratio 1:1. One half was further processed as follows: after a settling out time of 3 hours, the supernatant was decanted off and replaced by 300 g of methanol. The mixture was then stirred for about 45 min. After renewed settling out for 14 hours and decantation, 300 g of methanol were again added. The mixture was then stirred again for about 60 min. The mixture was then centrifuged at 5500 rpm for 30 min, and the supernatant was decanted off. The gel weight was 133 g.

The solids content of the gel was 78.7% (drying: 1 h at 130° C.). Elemental analysis revealed a zinc content of 72%, corresponding to 89.6% of ZnO. In addition, 0.17% of potassium, corresponding to about 0.43% of potassium acetate, and 0.15% of aluminium, corresponding to 0.31% of $Al_2O_3$, were found.

An X-ray diffractogram of the dried sample indicated exclusively hexagonal zinc oxide. Evaluation of the reflections according to Sherrer revealed an average crystallite size of 7.7 nm (reflections: 100 and 002, 100 doubly weighted since identical to 010 in the hexagonal crystalline system).

Example 4

770 ml of methanol were introduced into a 2l vessel having ground glass joints and fitted with a mechanical stirrer, condenser, thermometer and argon blanketing, and heated to 40° C. 284.91 g of zinc acetate dihydrate were then metered in and dissolved, and the solution was then heated to 60° C. The solution was slightly cloudy. After the addition of 4.60 g of sodium hydroxide pellets (98.8% strength), a clear solution was obtained. Then, over the course of 7 minutes, 173.29 g of aqueous sodium hydroxide solution (49.8% strength) were added, and the temperature increased to a maximum of 64° C. The solution immediately became cloudy, and a white Agitate formed, which was stirred for one hour at 60° C. The mixture was then cooled to room temperature. The volume of the mixture was 960 ml. After a settling out time of 14 h, the turbid supernatant was drawn off with suction, 750 ml of methanol were added to the sediment and the mixture was stirred for 30 minutes. After 4 hours, the precipitate had settled again, the clear supernatant was drawn off with suction, 750 ml of methanol were added to the sediment and the mixture was stirred for 30 minutes. After a further settling time of 14 h and withdrawal of the clear supernatant with suction, 250 ml of methanol were added to the sediment and the mixture was centrifuged for 10 minutes at 5500 rpm. 129.14 g of gel were obtained.

The solids content of the gel was 79.1% (dry residue: 1 h, 130° C.). The elemental analysis of the dry residue revealed a zinc content of 77.0%, corresponding to 95.8% of ZnO. The sodium content was 0.22%, corresponding to 0.78% of sodium acetate. The X-ray diagram of the gel dry residue indicated exclusively hexagonal ZnO. Evaluation of the reflections according to Scherrer revealed an average crystallite size of 9.4 nm.

Example 5

770 ml of methanol was introduced into a 2l vessel having ground glass joints and fitted with a mechanical stirrer, condenser, thermometer and argon blanketing, 122.30 g of zinc oxide (99.8%) were introduced, and the mixture was heated to 50° C. A solution of 183 g of glacial acetic acid (100% strength) and 27 g of water was then metered in over the course of 10 minutes, and the mixture was then heated to 60° C. A slightly turbid solution was formed. After the addition of 7.56 g of sodium hydroxide pellets (98.8% strength), the solution became as clear as water. The mixture was then cooled to 21° C. and, over the course of 60 seconds, 200.91 g of aqueous sodium hydroxide solution (49.5% strength) were added, and the temperature increased briefly to 51° C. The solution immediately became turbid and a white precipitate formed, which was stirred for one hour at 60° C. The mixture was then cooled to room temperature in iced water. The volume of the mixture was 1100 ml. The mixture was centrifuged for 30 minutes at 500 min$^{-1}$ without the precipitate thickening to give a gel. The supernatant was drawn off with suction, and the sediment was re ed with 750 ml of methanol by stirring for 15 min. The mixture was again centrifuged for 45 min at 500 min$^{-1}$, the clear supernatant was drawn off with suction and the sediment was again resuspended with 750 ml of methanol for 30 minutes. After centrifugation at 500 min$^{-1}$ for a further 45 minutes and removal of the clear supernatant with suction, the sediment was resuspended with 250 ml of methanol and thickened to give a gel by centrifuging for 10 minutes at 5200 min$^{-1}$. 168.5 g of gel were obtained.

The solids content of the gel was 74.1% (1 h, 130° C.). The elemental analysis revealed a zinc content of 78%, corresponding to 97.1% of ZnO. The sodium content was 0.870%, corresponding to 3.1% of sodium acetate. The X-ray diagram of the gel dry residue indicated exclusively hexagonal ZnO. Evaluation of the reflections according to Scherrer revealed an average crystallite size of 10.2 nm.

Example 6

Preparation of a Zinc Oxide Sol 134.1 g of dichloromethane were added to 134.1 g of the zinc oxide gel (B) prepared in Example 2 and occasionally shaken A transluscent sol (244.4 g) formed. Elemental analysis revealed a zinc content of 31%, corresponding to 38.6% of ZnO. By evaluating transmission electron micrographs of a sample of the sol diluted in an ethylene glycol/water mixture (FIG. 1, magnification 1,000,000:1), the average, circle-equivalent primary particle diameter of the zinc oxide particles was determined as 13 nm (number-average, from 283 counted particles).

Figure 2:
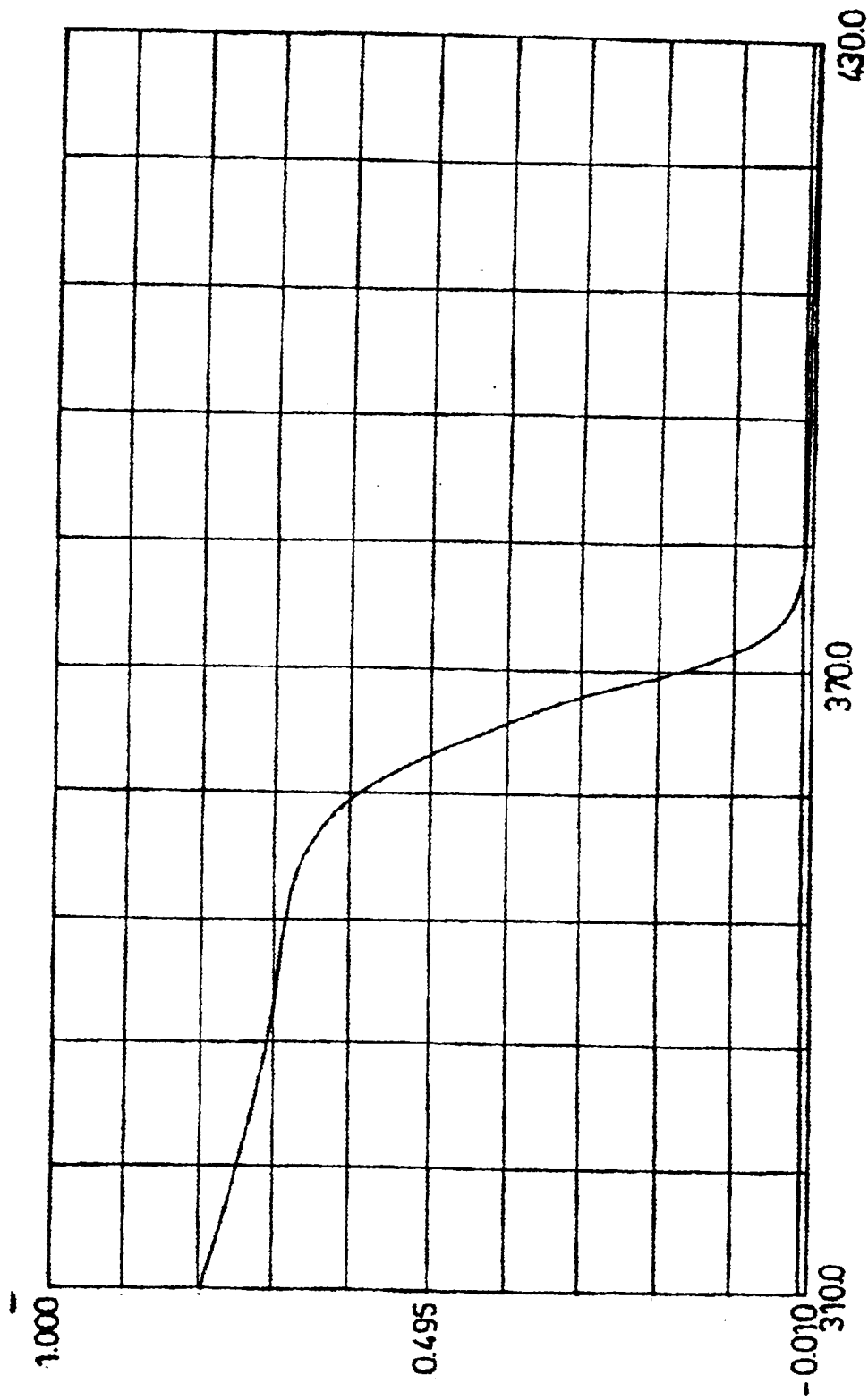
FIG. 2 is an optical absorption spectrum of the sol of Example 7.

Example 7
Preparation of a Zinc Oxide Sol 300 g of a zinc oxide gel prepared as in Example 1 were stirred with 291 g of ethylene glycol, 145 g of water and 82 g of triethanolamine. The methanol content of the gel was stripped off at room temperature under reduced pressure. 683 g of a yellowish transluscent sot were obtained. By evaluating transmission electron micrographs of a sample of the sol diluted in an ethylene glycol/water mixture, the average, circle equivalent primary particle diameter of the zinc oxide particles was defined as 10.2 m (number-average from 584 counted particles). The optical absorption spectrum of a sample of this sol diluted in an ethylene glycol/water mixture is shown in FIG. 2 (1: absorbance, 2: wavelength [nm]).

After a standing time of 3 months, the sol was externally unchanged. Redetermination of the average, circle-equivalent primary particle diameter of the zinc oxide particles by evaluating a transmission electron micrograph of a sample of the sol diluted in an ethylene glycol/water mixture revealed a value of 9.4 nm (number-average from 803 counted particles).

What is claimed is:

1. Process for the preparation of nano size zinc oxide particles, which are redispersible in organic solvents and/or water, comprising
   a) carrying out basic hydrolysis of at least one zinc compound in alcohol or an alcohol/water mixture, wherein the hydrolysis is carried out with substoichiometric amounts of base, based on the zinc compound, to form a precipitate;
   b) leaving the precipitate which initially forms during hydrolysis to mature until the zinc oxide has completely flocculated,
   c) thickening the precipitate to give a gel; and
   d) separating the gel from the supernatant phase;
   wherein the gel comprises nano sized zinc oxide particles having an average primary particle diameter of <15 nm, determined in a transmission electron micrograph.

2. The process of claim 1, wherein prior to, during or after precipitation, from 0.01 to 3 mol % of foreign ions, based on proportion of zinc, are added.

3. Process according to claim 1 wherein the zinc compound comprises at least one of zinc acetate and zinc acetate dihydrate.

4. Process according to claim 3, wherein the at least one of zinc acetate and zinc acetate dihydrate is prepared from zinc oxide in an upstream process.

5. The process of claim 1, wherein the gel is redispersed in organic solvents and/or water, optionally with the addition of surface-modifying compounds.

6. The process of claim 1, wherein the gel is redispersed by adding dichloromethane and/or chloroform.

* * * * *